US00PP08964P

United States Patent [19]

Tracy

[11] Patent Number: Plant 8,964

[45] Date of Patent: Nov. 1, 1994

[54] HYBRID TEA ROSE PLANT NAMED HILRED

[75] Inventor: Daniel L. Tracy, Richmond, Ind.

[73] Assignee: Hill's Floral Group, Richmond, Ind.

[21] Appl. No.: 924,621

[22] Filed: Jul. 31, 1992

[51] Int. Cl.[5] ..... A01H 5/00

[52] U.S. Cl. ..... Plt./21

[58] Field of Search ..... Plt. 29, 20, 21, 28

[56] References Cited

PUBLICATIONS

MacFarland (1980) *Modern Roses 8,* The McFarland Co, Harrisburg, Pa., p. 70.

*Primary Examiner*—Howard J. Locker
*Assistant Examiner*—E. F. McElwain
*Attorney, Agent, or Firm*—Tilton, Fallon, Lungmus & Chestnut

[57] ABSTRACT

A rose seedling intended for greenhouse culture and production of cut flowers, the new plant being of the tea rose class and particularly distinguished by its continuous production of medium high centered blossoms, its upright growth with little branching with medium diameter canes topped by long pointed bud of excellent red flower color.

1 Drawing Sheet

BACKGROUND OF THE NEW PLANT

This new variety of rose plant is a result of my crossing "Jacqueline" (U.S. Plant Pat. No. 2,183) with an undisseminated seedling #4-68R in the fall of 1979 at Richmond, Ind., with the object of producing a Hybrid Tea Rose. The varietal denomination of this new claimed cultivar is 'Hildred'. The claimed plant is also known as 2-80R.

The claimed plant was asexually reproduced through successive generations by grafting in Richmond, Ind., and at Livermore, Calif., showing that the distinctive characteristics of the claimed cultivar hold true and appear to be firmly fixed. This new variety can also be asexually propagated by budding, grafting, propagation from cuttings and micropropagation.

DESCRIPTION OF THE DRAWINGS

This new Hybrid Tea Rose is illustrated by the accompanying full color photographic drawing which shows buds in several stages of opening, a face view of a fully opened blossom, specimens of typical leaves, a specimen of young wood with new leaves, a specimen of wood and leaves with a newly formed bud, and typical specimens of mature wood.

DESCRIPTION OF THE NEW PLANT

The following is a detailed description of my new red rose variety based upon observations of specimens in our greenhouse at Richmond, Ind., in 1986, the color descriptions being according to the R.H.S. Colour Chart, (RHS), published by The Royal Horticultural Society of London, England.

THE PLANT

Origin: Seedling identified as #2-80R.
Parentage:
- *Seed parent.*—Jacqueline (U.S. Plant Pat. No. 2,183).
- *Pollen parent.*—Undisseminated seedling (H4-68R).

Classification: Hybrid Tea.
Type: Seedling for greenhouse culture and for cut flowers.
Form: Bush.

Growth (in greenhouse): Moderately free with upright and little branched habit.
Canes: Medium in diameter.
Main stem:
- *Length of main stem.*—18–24 inches.
- *Color.*—Green group 143-B (RHS).
- *Thorns.*—Several of medium length, hooked downward with a very narrow base. Color: greyed-/orange 165-B (RHS).

Prickles: Several greyed/orange 165-B (RHS).
Hairs: None.
Branches:
- *Color.*—Green group 143-C (RHS).
- *Thorns.*—Several of medium length, hooked downward with a very narrow base. Color: The tips of the thorns are RHS 146-C and the base of the thorns are RHS 180-A.

Prickles and hairs: None.
Foliage:
- *Quantity.*—Moderately sparse.
- *Leaves.*—Compound of five (5) to seven (7).
- *Leaflets. — size.*—Medium size.
- *Leaflets.*—Compound of five to seven leaflets. Shape ovoid with round base acute apex and serrated margin.
- *Appearance.*—Color: mature upper surface — green group 137-A (RHS), mature under surface — green group 137-C (RHS), young upper surface — green group 143-A (RHS), young under surfaces — green group 144-B (RHS). Rachis: medium with prickly, moderately hairy upper side and thorny under side. Stipules: medium length, narrow with short points turning out at an angle of less than 45 degrees toward the stem.

THE BUD

Before calyx breaks:
- *Size.*—Small.
- *Form.*—Short pointed without conspicuous neck; foliaceous appendage on the surface of the bud with slender foliaceous parts extending beyond the tip of the bud equal to $\frac{1}{4}$ or more of its length.
- *Color of calyx.*—Yellow green group 144A (RHS).

As calyx breaks:

*Outside petal color.*—Red group 53-A (RHS).

As first petal opens:

*Size.*—Medium small.

*Form.*—Long pointed.

*Color of petal.*—Outside: red group 46-C (RHS). Inside: red group 45-B (RHS).

Opening: The bud opens well in a greenhouse.

Sepals:

*Inside color.*—Yellow/green group 146B (RHS).

*Outside color.*—Yellow green group 146-C (RHS).

Peduncle: Medium length, medium diameter and medium strong with bark entirely smooth.

*Bark.*—Yellow/green group 145-A (RHS).

*Thorns, prickles and hairs.*—None.

THE FLOWER

Blooming habit: Continuous in a greenhouse with a moderate production of buds.

Borne: 2 to a stem; sometimes 3 in irregular clusters on long, moderately strong stems.

Size: Medium 3½ to 4 inches in diameter.

Form: High centered at first, then becoming open with the petals remaining rolled outward. At maturity, the petals become loosely rolled when fully opened.

*Shape.*—Outside petals, oval with apex mucronate with one notch, intermediate petals obovate with apex mucronate with one notch and outside petals, obovate with apex mucronate with one notch.

*Aspect.*—Thick.

*Appearance.*—Inside velvety, outside satiny.

Color: A. The following is a color description of a newly opened greenhouse flower grown in the month of December.

*Outside petals.*—Outer surface — red group #45-A (RHS). Inside surface — red group #46-C (RHS).

*Intermediate petals.*—Outer surface — red group #46-B (RHS). Inside surface — red group #59-A (RHS).

*Inner petals.*—Outer surface — red group #46-A (RHS). Inside surface — red group #45-A (RHS).

B. The following description was made from a rose that was open for three (3) days in a greenhouse during the month of July, 1987, in, Richmond, Ind.

*Outside petals.*—Outer surface — red group #45-A (RHS). Inside surface — red group #46-A (RHS).

*Intermediate petals.— Outer surface — red group* #46-A (RHS). Inside surface — red group #45-A (RHS).

*Inner petal.*—Outer surface — red group #46-A (RHS). Inside surface — red group #45A (RHS).

Fragrance: Moderate in greenhouse.

Persistence: Petals persist in greenhouse.

Effect of weather: Slight drop of production in the Winter months.

Flower longevity: Greenhouse cut flowers about eleven (11) days at living room temperature in December.

Disease resistance: Slight resistance to mildew and botyritis.

REPRODUCTIVE ORGANS

Stamens: Few, arranged regularly around pistils.

*Filaments.*—Short length, many with anthers. Color of filaments — red group #48-A (RHS).

*Anthers.*—Small, open at various times. Color of anthers — yellow/orange #16-C (RHS).

*Pollen.*—Moderate. Color of pollen — yellow-/orange #22-A (RHS).

Pistils:

*Number.*—Medium.

*Styles.*—Uneven, short, thin, separated. Color of styles — red group #53-C (RHS) at base, yellow/orange group #16-D (RHS).

Stigmas.—Color — yellow/white group #158C (RHS).

Ovaries: Some protruding from hip.

Hips: Short, oblong with inconspicuous neck; pear-shaped; very smooth.

Sepals:

*Inside color.*—Yellow/green group #146-B (RHS).

*Outside color.*—Yellow/green group #146-C (RHS).

Seeds: Few, small seeds.

This new rose plant cultivar is a superior plant when it is judged on its long pointed bud form and its clear, bright red color makes it an improvement over seed parent "Jacqueline" (U.S. Plant Pat. No. 2,183). It is better than its pollen parent in productivity and keeping qualities. The claimed plant most closely resembles Hybrid Tea Rose plant named Buram (U.S. Plant Pat. No. 7,052) (hereinafter "Buram") and Rose plant Arotrusim (U.S. Plant Pat. No. 7,157) (hereinafter "Arotrusim"). The average size of the flowers of Buram and Arotrusim are larger than that of the claimed plant. Both the claimed rose and Arotrusim bloom continuously in a greenhouse where Buram blooms only recurrently. Furthermore, the bud of the claimed rose is short and pointed without a conspicuous neck whereas the bud of Buram is ovoid and high centered and the bud of Arotrusim is long and pointed. The color of the foliage of the claimed plant is green whereas in Buram the old foliage is purplish green and the new foliage is yellow green. The old foliage of Arotrusim is reddish brown and the new foliage is matt green. Both Buram and Arotrusim are disease resistant and have some winter hardiness. The claimed cultivar is not disease or frost resistant.

I claim:

1. A new and distinct Hybrid Tea Rose cultivar, substantially as herein shown and described, characterized by its long pointed buds, the clear bright red color of the flower petals, and by its moderately free and continuous flower production under greenhouse culture.

* * * * *

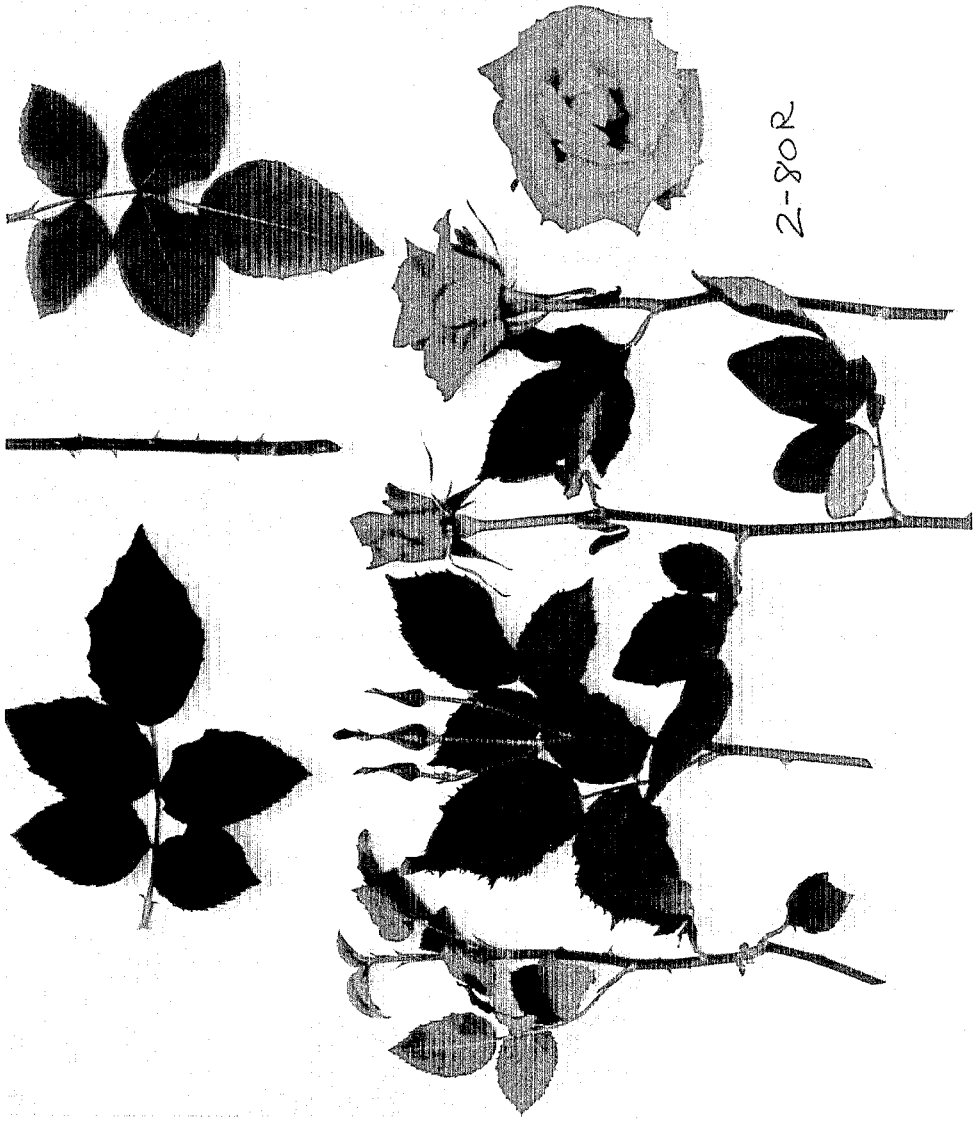
2-80R